US00PP16093P2

(12) United States Plant Patent
Olesen et al.

(10) Patent No.: US PP16,093 P2
(45) Date of Patent: Nov. 1, 2005

(54) ***CLEMATIS* PLANT NAMED 'EVIPO036'**

(50) Latin Name: *Clematis viticella*
Varietal Denomination: Evipo036

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 85 days.

(21) Appl. No.: 10/927,722

(22) Filed: Aug. 27, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses. With a tall growth habit, profuse, nodding pink flowers, continuous summer flowering and good disease resistance. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: *Clematis* I. Genus—*Clematis*. Species—*viticella*.
Variety denomination: 'Evipo036'.

SUMMARY OF THE DISCOVERY

The present invention constitutes a new and distinct variety of *Clematis* which originated as a chance seedling of unknown parents. The new variety is named 'Evipo036'.

The objective of the selection of this *Clematis* variety for commercial glasshouse and nursery culture was to create a new and distinct variety with unique qualities that this variety has:

1. Profuse nodding pink flowers;
2. Reliable and repeatable production plant;
3. Summer flowering;
4. Good disease resistance.

These qualities required improvement in *Clematis* varieties that were in commercial cultivation and the objectives have been substantially achieved in the new variety, as evidenced by the unique combination of characteristics that are present in 'Evipo036', which distinguish it from all other varieties of which we are aware.

Evaluations of the seedling plant, which was discovered in a cultivated area, were conducted in a controlled environment. As a result, 'Evipo036' was selected by Raymond J. Evison and Mogens N. Olesen in their *Clematis* development program in Domarie Vineries Les Sauvagees, St. Sampsons, Guernsey, Channel Islands, United Kingdom in June 1996.

Asexual reproduction of 'Evipo036' by cuttings was first done by Raymond J. Evison and Mogens N. Olesen in Domarie Vineries Les Sauvagees, St. Sampsons, Guernsey, Channel Islands, United Kingdom in April 1997. This initial and subsequent asexual propagations have demonstrated that the characteristics of 'Evipo036' are true to type and are transmitted from one generation to the next.

BRIEF DESCRIPTION OF THE DRAWING

The accompanying color illustrations show as true as is reasonably possible to obtain in color photographs of this type:

FIG. 2.2 Stem showing branching and the attachment of leaves and flower buds;

FIG. 2.3 Flower bud at various stages of opening;

FIG. 2.4 Stem showing attachment of mature and juvenile leaves;

DETAILED DESCRIPTION OF THE VARIETY

Figure 1:
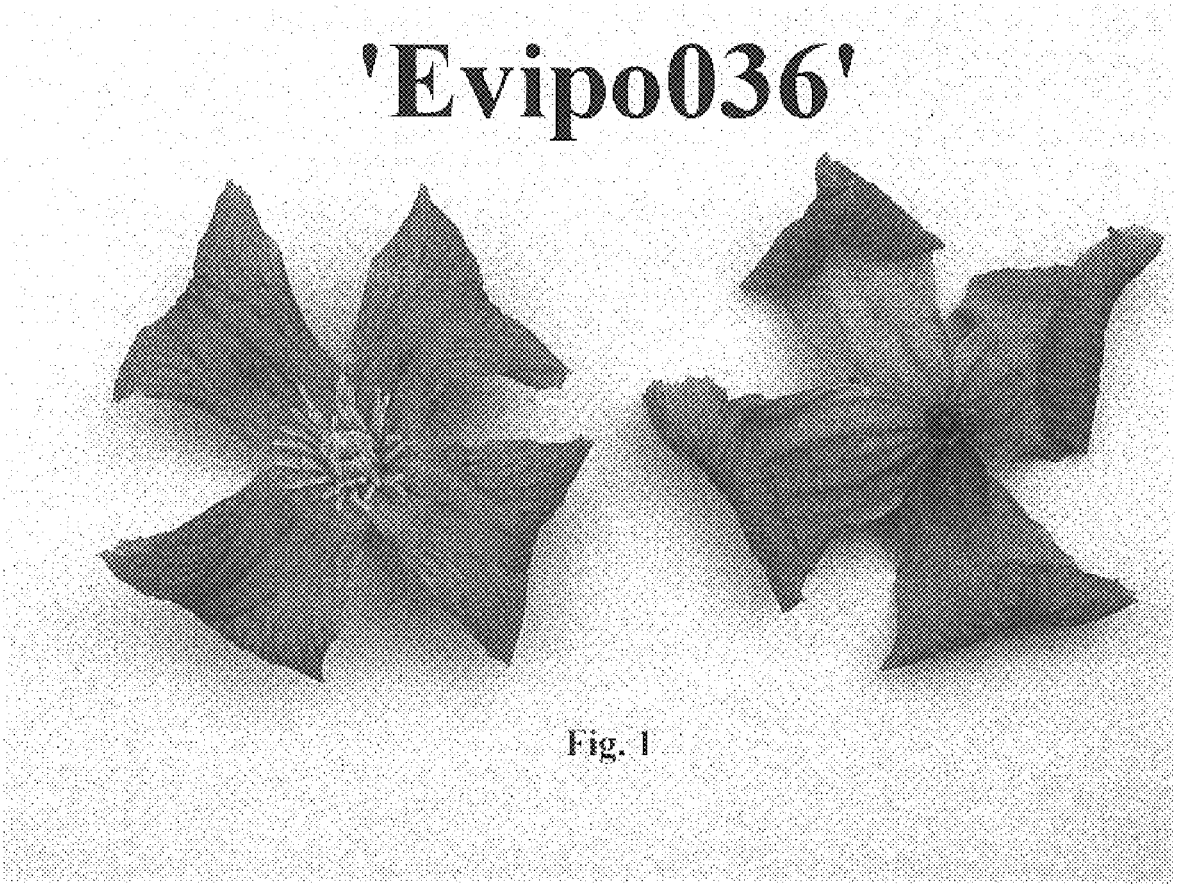
FIG. 1 Enlarged image of open flower, upper and lower surface.

The following is a detailed description of 'Evipo036', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Etoile Rose', a non-patented variety. Chart 1 details several physical characteristics of 'Evipo036' and the comparison variety.

CHART 1

| | 'Evipo036' | 'Etoile Rose' |
|---|---|---|
| Disease resistance | Good general resistance to fungal diseases and not specifically prone to mildew | Prone to powdery mildew |
| Flower form | Open & campanulate | Long & campanulate |

FLOWER AND FLOWER BUD

Blooming habit: Summer flowering. Normal flowering months are May, June, July, August, September.

Flower bud:

*Size.*—12 mm to 16 mm length by 7 mm diameter.

*Bud form.*—Elliptical.

*Bud color.*—Red-Purple Group 71B.

Peduncle:

*Aspects.*—Normally horizontal and the flower is held facing downwards (nodding).

*Surface.*—Smooth.

*Length.*—140 to 160 mm.

*Color.*—Green-Yellow Group 143B changing to Red-Purple Group 71A as the flower opens.

*Strength.*—Weak.

Receptacle: Absent.

Flower arrangement:

*Location on vine.*—Flowering normally occurs on new growth.

*Borne.*—Compound cyme cluster of 3 to 5 flowers.

Flower bloom:

*Size.*—68 to 72 mm in diameter. 15 to 18 mm in depth.

*Profile.*—Single. Upon opening: Flowers are campanulate. After opening: Campanulate with tepals reflexing strongly.

*Tepal color.*—Upon opening: Upper surface: Violet Group 86A. After opening: Upper surface: Red-Purple Group N74B. Lower surface: Red-Purple Group N74C.

*Variations.*—Purple Group 75C observed at tepal base. Tepal veins are Red-Purple Group 72A.

*Fragrance.*—None.

*Lasting quality on plant.*—10 to 15 days.

*Lasting quality as a cut flower.*—4 to 5 days.

Tepals:

*Quantity.*—Normally 4 tepals.

*Size.*—40 mm to 45 mm (l)×18 to 20 mm (w).

*Shape.*—Individual tepal shape is oblanceolate.

*Margin.*—Entire, medium undulation.

*Tepal apex.*—Notched and blunt.

*Recurvature of tip.*—Very strongly reflexed.

*Persistence.*—Tepals drop off cleanly.

*Arrangement.*—Tepals are arranged regularly.

Reproductive organs:

*Arrangement.*—Medium.

*Pollen.*—Quantity: Below average. Color: Yellow Group 12D.

*Anthers.*—Size: 4 mm in length. Color: Yellow Group 16D. Quantity: 30 to 50.

*Filaments.*—Color: White Group N155A. Length: 6 mm.

*Pistils.*—Quantity: 20 to 30.

*Stigmas.*—Inferior to anthers, becoming superior as the flower opens.

*Styles.*—Color: Greyed-Yellow Group 162A. Length: 10 mm.

Seed head characteristics:

*Diameter.*—30 mm.

*Seed shape.*—Tear shaped.

*Seed size.*—4 to 5 mm (l)×3.5 mm (w) with a plumose tail of length 10 to 14 mm.

PLANT

Plant form: Climbing.

Size: 2 to 2.5 meters in height. Average spread is 1 to 1.5 meter.

Hardiness: Trials to date show the variety hardy in USDA cold hardiness Zones 4.

Stems:

*Color.*—Young wood: Greyed-Orange Group 177A. Older wood: Greyed-Orange Group N167A.

*Internodes.*—Shape: Cylindrical. Length: 120 to 190 mm.

*Surface.*—Young wood: Smooth and somewhat pubescent. Older wood: Smooth and somewhat pubescent.

Plant foliage:

*Leaf characteristics.*—Deciduous.

*Mature leaf form.*—Trifoliate, normally 3 to 7 leaflets emanate from a central rachis in thyrsiform fashion.

*Compound leaf size.*—125 to 170 mm (l)×100 to 150 mm (w).

*Abundance.*—Generally there are 12 compound leaves per 1000 mm of stem.

*Color.*—Upper surfaces of mature leaves: Green Group 141A. Lower surfaces of mature leaves: Green Group 141C. Upper surfaces of new foliage: Yellow-Green Group 141B. Lower surfaces of new foliage: Yellow-Green Group 141C.

Plant leaves and leaflets:

*Stipules.*—Absent.

*Petioles.*—Average length: 60 to 100 mm. Color: Yellow-Green Group 146A. Clasping: By leaf petiole.

*Petioloule.*—Length: 7 to 20 mm. Color: Yellow-Green Group 146A.

*Leaflet shape.*—General shape: Elliptic and ovate. Base: Rounded and attenuate. Apex: Rounded and acute. Margin: Entire.

*Leaflet size.*—12 to 15 mm in length by 6 to 10 mm wide.

*Leaflet texture.*—Upper side: Smooth. Lower side: Smooth. Pubescent: No. Thickness: Moderate. Glossiness: Moderately glossy.

Disease resistance: Subject to any disease that normally attacks the species. However, the variety is more tolerant to *Botrytis, Phoma clematadina*, and root diseases such as Theilaviopsis. Plant is also more resistant to mildew than other *Clematis* of the similar flower color and form.

We claim:

1. A new and distinct variety of *Clematis* plant named 'Evipo036', described and illustrated herein, due to its abundant nodding pink flowers, attractive long-lasting foliage and repeatable flowering under glasshouse conditions, suitability for production from softwood cuttings in pots, durable flowers and foliage which make the variety suitable for distribution in the floral industry.

* * * * *

Figure 2:
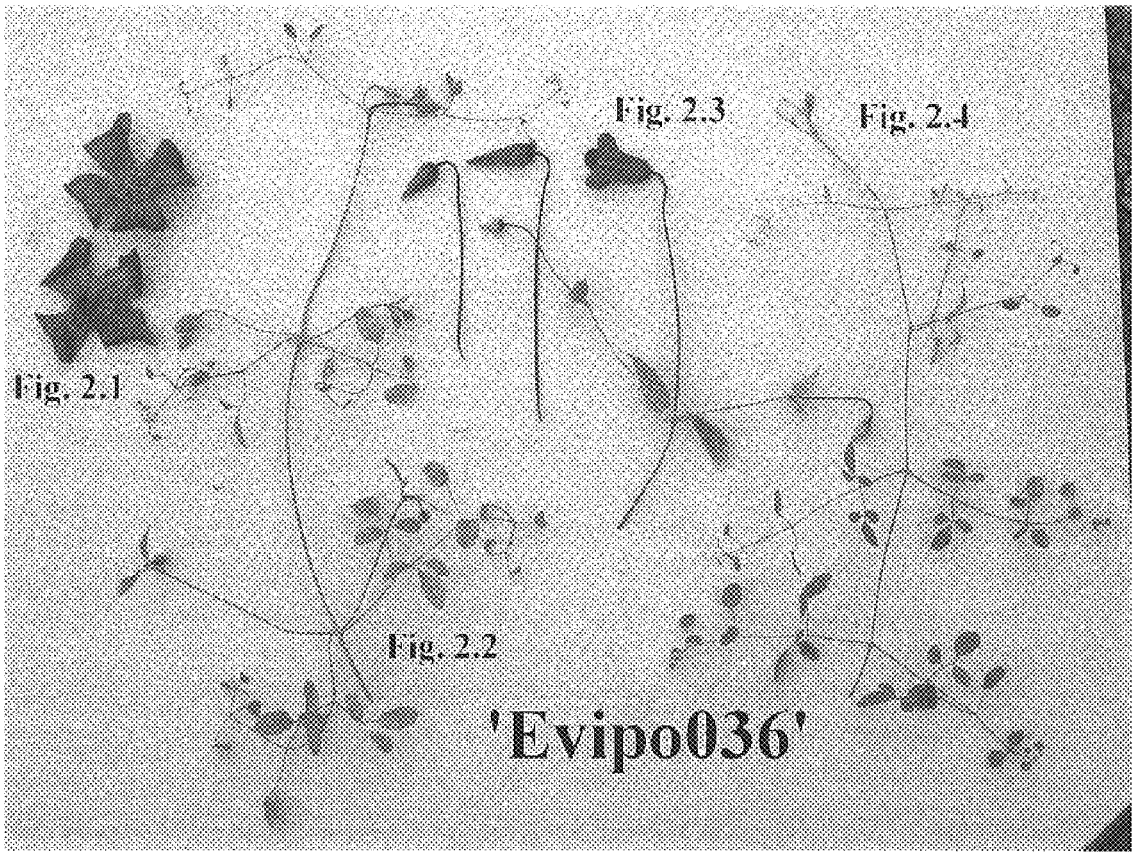
FIG. 2.1 Open flower, upper and lower surface.
Figure 3:
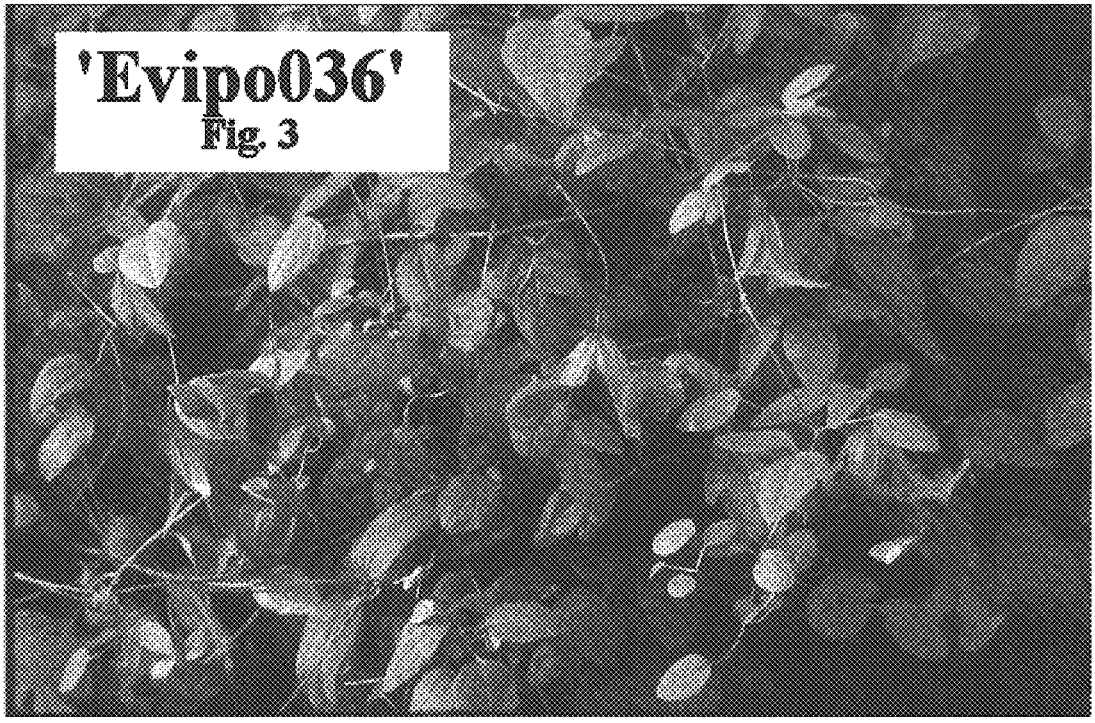
FIG. 3 Cluster of flowers and leaves.

Fig. 2.3
Fig. 2.4
Fig. 2.1
Fig. 2.2
'Evipo036'